United States Patent [19]

Schirmer et al.

[11] Patent Number: 4,569,689
[45] Date of Patent: Feb. 11, 1986

[54] ANILINE DERIVATIVES AND THEIR USE FOR CONTROLLING UNDESIRABLE PLANT GROWTH

[75] Inventors: Ulrich Schirmer, Heidelberg; Norbert Goetz, Worms; Bruno Wuerzer, Otterstadt, all of Fed. Rep. of Germany

[73] Assignee: BASF Aktiengesellschaft, Fed. Rep. of Germany

[21] Appl. No.: 620,562

[22] Filed: Jun. 14, 1984

[30] Foreign Application Priority Data

Jun. 15, 1983 [DE] Fed. Rep. of Germany ....... 3321582

[51] Int. Cl.⁴ ............... C07C 127/19; A01N 47/30
[52] U.S. Cl. ............................ 71/88; 71/95; 71/94; 71/111; 71/100; 71/118; 71/120; 564/52; 564/53; 564/54; 564/123; 564/213; 564/219; 564/191; 564/189; 564/190; 564/202; 564/212; 260/455 A; 260/239 A; 260/239 B; 260/453 RW; 560/28; 548/530; 548/240; 544/63; 544/162; 544/168; 546/229
[58] Field of Search ............... 564/52, 53, 54, 27, 564/222, 191, 123, 189, 190, 202, 212, 213, 219; 71/120, 111, 100, 118, 88, 95, 94; 260/455 A, 239 A, 239 B, 453 RW; 560/28; 548/530, 240; 544/63, 162, 168; 546/229

[56] References Cited

U.S. PATENT DOCUMENTS

| | | | |
|---|---|---|---|
| 2,913,322 | 11/1959 | Beaver et al. | 71/2.5 |
| 3,757,016 | 9/1973 | Hunter et al. | 260/247.2 B |
| 4,405,358 | 9/1983 | Schirmer et al. | 71/98 |
| 4,422,871 | 12/1983 | Schirmer et al. | 71/120 |
| 4,437,880 | 3/1984 | Takahashi et al. | 71/120 |

FOREIGN PATENT DOCUMENTS

| | | | |
|---|---|---|---|
| 1332371 | 6/1963 | France | 71/120 |
| 1417322 | 2/1973 | United Kingdom . | |
| 1542207 | 4/1977 | United Kingdom . | |

Primary Examiner—Thomas A. Waltz
Assistant Examiner—R. A. Picard
Attorney, Agent, or Firm—Keil & Weinkauf

[57] ABSTRACT

Aniline derivatives of the formula

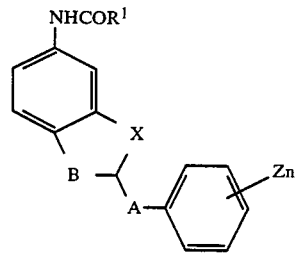

where $R^1$ is alkoxy, alkylthio, unsubstituted or substituted cycloalkoxy or the radical $-NR^2R^3$, X is $-CH_2-$, $-CH(OH)-$ or $-CO-$, A is an unsubstituted or substituted alkylene chain, B is unsubstituted or substituted methylene or dimethylene, Z is hydrogen, halogen, alkyl, alkoxy, haloalkyl or haloalkoxy, and n is 1, 2 or 3, are used for controlling undesirable plant growth.

9 Claims, No Drawings

ANILINE DERIVATIVES AND THEIR USE FOR CONTROLLING UNDESIRABLE PLANT GROWTH

The present invention relates to aniline derivatives, herbicides which contain these compounds as active ingredients, and a process for controlling undesirable plant growth with these compounds.

It is known that N-methoxy-N-methyl-N'-phenylureas possess herbicidal activity.

We have found that aniline derivatives of the formula

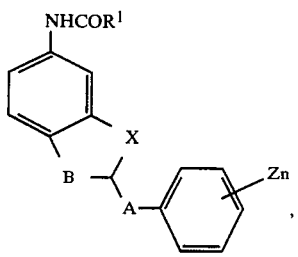

where $R^1$ is $C_1$-$C_4$-alkoxy or $C_1$-$C_4$-alkylthio or is $C_1$-$C_4$-alkyl which is unsubstituted or substituted by halogen or by $C_1$-$C_5$-alkoxy, or is $C_3$-$C_6$-cycloalkyl, $C_3$-$C_6$-cycloalkoxy or the radical —$NR^2R^3$ where $R^2$ and $R^3$ independently of one another are each hydrogen, $C_1$-$C_4$-alkyl, $C_1$-$C_4$-alkoxy, $C_3$-$C_6$-cycloalkyl or $C_3$-$C_6$-cycloalkoxy, or $R^2$ and $R^3$ together form an alkylene chain of not more than 6 carbon atoms which is unsubstituted or substituted by methyl and may or may not contain oxygen as a chain member, X is methylene, —CH(OH)— or —CO—, A is an alkylene chain of 1 to 5 carbon atoms which is unsubstituted or substituted by alkyl of 1 to 5 carbon atoms, B is methylene or dimethylene which is unsubstituted or substituted by alkyl of 1 to 3 carbon atoms, Z is hydrogen, halogen, $C_1$-$C_6$-alkyl, $C_1$-$C_6$-alkoxy, $C_1$-$C_6$-haloalkyl or $C_1$-$C_6$-haloalkoxy, and n is 1, 2 or 3, have a herbicidal action and are well tolerated by a number of crops.

The substituents of the formula I can have the following meanings:

$R^1$ is $C_1$-$C_4$-alkoxy or $C_1$-$C_4$-alkylthio or is $C_1$-$C_5$-alkyl which is unsubstituted or substituted by halogen or by $C_1$-$C_5$-alkoxy, eg. methoxy, ethoxy, n-propoxy, isopropoxy, sec-butoxy, tert.-butoxy, n-pentyloxy, methylthio, ethylthio, n-propylthio, sec-butylthio, tert.-butylthio, methyl, ethyl, n-propyl, n-butyl, sec-butyl, tert.-butyl, isobutyl, n-pentyl, chloromethyl, 1,1-dichloroethyl, dichloromethyl, trichloromethyl, methoxymethyl, 1-methoxyethyl or 2-methoxyethyl, $C_3$-$C_6$-cycloalkyl, eg. cyclopropyl, cyclopentyl or cyclohexyl, $C_3$-$C_6$-cycloalkoxy, eg. cyclohexyloxy, or the radical —$NR^2R^3$, where $R^2$ and $R^3$ independently of one another are each hydrogen, $C_1$-$C_4$-alkyl or $C_1$-$C_4$-alkoxy, eg. methyl, ethyl, isopropyl, n-butyl, sec-butyl, isobutyl, tert.-butyl, methoxy or ethoxy, $C_3$-$C_6$-cycloalkyl, eg. cyclopropyl, cyclopentyl or cyclohexyl, or $C_3$-$C_6$-cycloalkoxy, eg. cyclohexyloxy, or $R^2$ and $R^3$ together form an alkylene chain of not more than 6 carbon atoms which is unsubstituted or substituted by methyl and may or may not contain oxygen as a chain member, eg. trimethylene, tetramethylene, 1,4-dimethyltetramethylene, pentamethylene, hexamethylene, 3-oxapentamethylene, 1-oxapentamethylene or 1-oxatetramethylene.

A is an alkylene chain of 1 to 5 carbon atoms, which can be substituted by $C_1$-$C_5$-alkyl, in particular by methyl, eg. —$CH_2$—, —$CH(CH_3)$—, —$(CH_2)_3$—, —$(CH_2)_2$—, —$CH_2CH(CH_3)CH_2$—, —$CH(_2)_5$— or —$CH_2CH(CH_3)(CH_2)_3$—.

B is methylene or dimethylene which is unsubstituted or substituted by $C_1$-$C_3$-alkyl, in particular by methyl, eg. —$CH_2$—, —$CH(CH_3)$—, —$(CH_2)_2$—, —$CH(CH_3)CH_2$— or —$CH_2CH(CH_3)$—.

Z is hydrogen, halogen, eg. fluorine, chlorine or bromine, $C_1$-$C_6$-alkyl, $C_1$-$C_6$-alkoxy, $C_1$-$C_6$-haloalkyl or $C_1$-$C_6$-haloalkoxy, eg. methyl, ethyl, isopropyl, tert.-butyl, n-hexyl, methoxy, ethoxy, isopropoxy, tert.-butoxy, n-hexyloxy, trifluoromethyl, 1,1,2-trifluoro-2-chloroethoxy or difluoromethoxy. Z is in the ortho, meta or para position with respect to A. n is preferably 1 but may furthermore be 2 or 3, particularly when Z is fluorine, chlorine, bromine or methyl.

Preferred compounds of the formula I are those in which $R^1$ is —$N(CH_3)(OCH_3)$, A and X are each methylene, B is methylene or dimethylene, Z is hydrogen, halogen, in particular chlorine, or $C_1$-$C_4$-alkyl or $C_1$-$C_4$-alkoxy, in particular methyl or methoxy, and n is 1.

The aniline derivatives of the formula I are obtained by reacting an amine of the formula

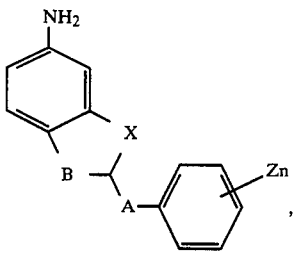

where A, X, B, Z and n have the above meanings, with a compound of the formula

where $R^1$ has the above meanings and X is a leaving group, preferably halogen, eg. chlorine or bromine, or $R^1$—CO—O—.

The reaction is carried out in the presence of an inert organic solvent, suitable solvents being ethers, such as tetrahydrofuran, dimethoxyethane, diethyl ether or methyl tert.-butyl ether, esters, such as ethyl acetate, aliphatic or aromatic hydrocarbons and aliphatic or aromatic chlorohydrocarbons, such as toluene, dichloromethane or pyridine. Mixtures of these solvents can also be used. The amount of solvent is from 100 to 5000% by weight, based on the amine of the formula II.

The reaction is advantageously carried out in the presence of an acid acceptor, suitable ones being alkali metal hydroxides, alkali metal carbonates, alkali metal bicarbonates, alkaline earth metal hydroxides, alkaline earth metal carbonates, alkaline earth metal bicarbonates, alkaline earth metal oxides and amines, eg. sodium bicarbonate, potassium carbonate, triethylamine, pyridine, N,N-dimethylaniline, N,N-dimethyl-N-cyclohexylamine or quinoline. The amount of acid acceptor is from 1 to 4 moles per mole of the compound of the formula III.

The starting materials of the formulae II and III are preferably reacted with one another in equimolar amounts, and the reaction temperature is from 0° to 80° C., preferably from 20° to 30° C.

The amines of the formula II are novel. They are obtained by a conventional method, by aldol condensation followed by hydrogenation. For example, an unsubstituted or substituted nitro-alpha-indanone or nitro-alpha-tetralone is reacted with an unsubstituted or substituted benzaldehyde to give a nitrochalcone (R. J. Murray and N. A. Cromwell, J. Org. Chem. 41 (1976), 3540-3545):

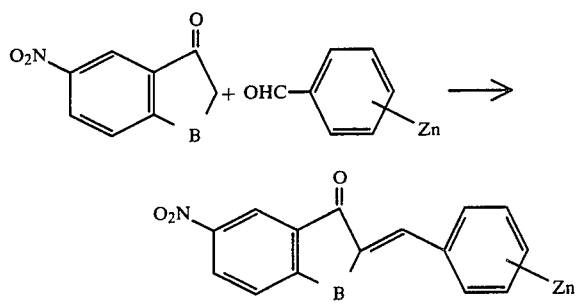

The resulting nitrochalcone is hydrogenated in a conventional manner, in an acetic acid/sulfuric acid mixture (where X is methylene) or in an organic solvent, such as methanol or tetrahydrofuran (where X is —CO— or —CH(OH)—), in the presence of palladium on carbon or of Raney nickel, at from 0° to 150° C., preferably from 20° to 80° C., under atmospheric or superatmospheric pressure. In the formulae, B, Y, Z and n have the above meanings.

Amines of the formula II in which A is —CH₂CH(CH₃)CH₂— or —(CH₂)₃— are obtained by condensing unsubstituted or substituted nitro-alpha-tetralone or nitro-alpha-indanone with an unsubstituted or substituted cinnamaldehyde in accordance with the equation

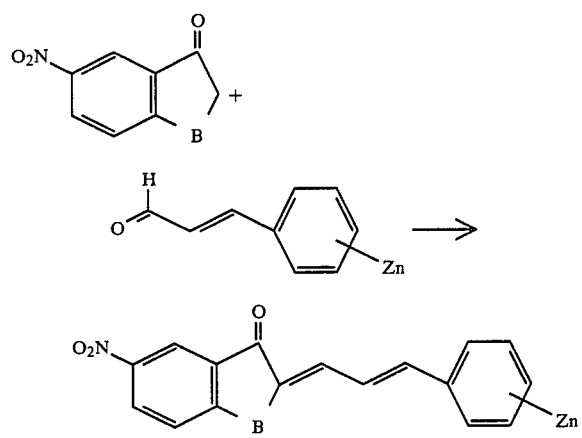

and then hydrogenating the product.

The absorption of hydrogen in the hydrogenation of the above nitrophenylchalcone takes place stepwise. When the reacting is carried out in tetrahydrofuran, absorption of hydrogen can be either terminated when the stage of the saturated anilinoketone (X=—CO—) is reached, or continued until the anilinocarbinol stage (X=—CH(OH)—) is attained; when the reaction is carried out in an acetic acid/sulfuric acid mixture, hydrogenation can be continued directly to the anilino-hydrocarbon stage (X=—CH₂—).

The hydrogenation is carried out in a conventional manner in the presence of Raney nickel or, preferably, palladium on active carbon. In this case, hydrogenation to the saturated anilinoketone (X=—CO—) takes place at as low as 0°-30° C., preferably 25° C., and under from 1.0 to 20, preferably 1.1, bar. Prolonging the reaction time, increasing the hydrogenation temperature and/or increasing the pressure to as much as 50 bar results in the keto group being reduced to the carbinol group (X=—CH(OH)—) (Houben-Weyl, Methoden der Org. Chemie, vol. 4/1c, page 13 et seq., Georg Thieme Verlag, Stuttgart, 1980).

The Examples which follow illustrate the synthesis of the amines of the formula II:

EXAMPLE A 72 g of 7-nitro-α-tetralone, 40 g of benzaldehyde and 10 g of boric acid in 500 ml of xylene were boiled for 18 hours, water being separated off. The still hot solution was stirred into toluene, and the mixture was cooled and then filtered under suction. 84.9 g (yield: 81%) of 7-nitrobenzylidene-α-tetralone of melting point 164°-166° C. were obtained.

84 g of 7-nitrobenzylidene-α-tetralone were dissolved in 30 g of sulfuric acid and 1000 ml of glacial acetic acid, 5 g of palladium/active carbon (10% strength) were added, and hydrogenation was carried out under 1.1 bar at 70° C. until 43.5 l of hydrogen had been absorbed. The mixture was then filtered, the filtrate was evaporated down and the residue was rendered alkaline with 10% strength sodium hydroxide solution and extracted by shaking with diethyl ether. The organic phase was dried over sodium sulfate and filtered, and the filtrate was distilled to give 52.7 g (yield: 74%) of the amine of the formula

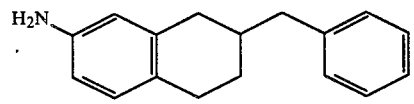

of boiling point 162°-164° C./0.7 mbar.

EXAMPLE B 118 g of 7-nitro-(4'-chlorobenzylidene)-α-tetralone were dissolved in 1000 ml of tetrahydrofuran, and hydrogenation was carried out in the presence of 4 g of 10% strength palladium/animal charcoal at from 20° to 25° C. under 1.1 bar, until 33.5 l of hydrogen had been absorbed. After drying over sodium sulfate, the mixture was filtered and evaporated down. The residue obtained was recrystallized from acetonitrile to give 51.7 g (yield: 48%) of the amine of the formula

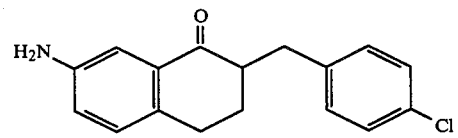

of melting point 168°-170° C.

The following amines of the formula II can be prepared by a similar method:

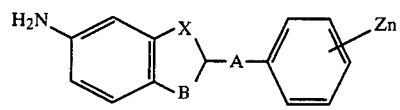

| A | B | X | Zn | m.p. [°C] |
|---|---|---|---|---|
| —CH₂— | —CH₂—CH₂— | —CO— | H | 98–100 |
| —CH₂— | —CH₂—CH₂— | —CH(OH)— | H | 120–125 |
| —CH₂— | —CH₂— | —CO— | H | 149–151 |
| —CH₂— | —CH₂—CH₂— | —CH₂— | H | 52–54 |
| —CH₂— | —CH₂—CH₂— | —CH₂— | 4-Cl | 71–73 |
| —CH₂— | —CH₂—CH₂— | —CH₂— | 4-F | 71–75 |
| —CH₂— | —CH₂—CH₂— | —CH₂— | 4-CH₃ | 90–92 |
| —CH₂— | —CH₂—CH₂— | —CH₂— | 4-OCH₃ | 83–86 |
| —CH₂— | —CH₂—CH₂— | —CH₂— | 3,4-(CH₃)₂ | |
| —CH₂— | —CH₂—CH₂— | —CH₂— | 4-t-C₄H₉ | |
| —CH₂— | —CH₂—CH₂— | —CH₂— | 3-CF₃ | |
| —CH₂— | —CH₂—CH₂— | —CH₂— | 4-OCHF₂ | |
| —CH₂— | —CH₂—CH₂— | —CH₂— | 4-O—n-C₆H₁₃ | |
| —CH₂—CH₂—CH₂— | —CH₂—CH₂— | —CH₂— | H | 48–50 |
| —CH₂—CH₂—CH₂— | —CH₂—CH₂— | —CO— | H | 55–58 |
| —CH₂— | —CH₂—CH₂— | —CO— | 4-F | |
| —CH₂— | —CH₂—CH₂— | —CO— | 4-CH₃ | 113–117 |
| —CH₂— | —CH₂—CH₂— | —CO— | 4-OCH₃ | 135–138 |
| —CH₂— | —CH₂—CH₂— | —CO— | 3,4-Cl₂ | |
| —CH₂— | —CH₂—CH₂— | —CO— | 3-Cl | |
| —CH₂—CH(CH₃)—CH₂— | —CH₂—CH₂— | —CH₂— | H | |
| —(CH₂)₅ | —CH₂—CH₂— | —CH₂— | H | |

The Example which follows illustrates the preparation of the aniline derivatives of the formula I.

EXAMPLE 1

10.7 g of 2-benzyl-7-amino-1,2,3,4-tetrahydronaphthalene (Example A) were dissolved in 150 ml of tetrahydrofuran, 4.6 g of sodium bicarbonate were added, and the mixture was reacted with 5.6 g of N-methoxy-N-methylcarbamyl chloride at from 20° to 25° C., while stirring thoroughly. Stirring was continued for 12 hours, after which the mixture was filtered, the filtrate was evaporated down, the residue was triturated with petroleum ether, and the product was filtered off under suction, giving 11.6 g (yield: 79.5%) of the aniline derivative of the formula

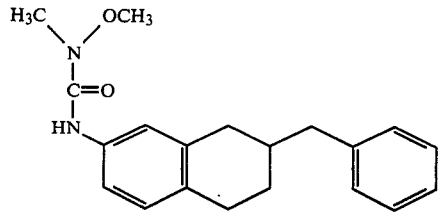

of melting point 118°–120° C.

The following compounds of the formula I can be prepared by a similar method:

| | R¹ | A | B | X | Zn | M.p. [°C] |
|---|---|---|---|---|---|---|
| 2 | C₂H₅ | —CH₂— | —CH₂—CH₂— | —CH₂— | H | 85–87 |
| 3 | N(CH₃)₂ | —CH₂— | —CH₂—CH₂— | —CH₂— | H | 142–144 |
| 4 | SCH₃ | —CH₂— | —CH₂—CH₂— | —CH₂— | H | 85–89 |
| 5 | cyclopropyl | —CH₂— | —CH₂—CH₂— | —CH₂— | H | 162–165 |
| 6 | —NHCH₃ | —CH₂— | —CH₂—CH₂— | —CH₂— | H | |
| 7 | N(OC₂H₅)C₂H₅ | —CH₂— | —CH₂—CH₂— | —CH₂— | H | |
| 8 | morpholino (O-N ring) | —CH₂— | —CH₂—CH₂— | —CH₂— | H | |
| 9 | t-C₄H₉ | —CH₂— | —CH₂—CH₂— | —CH₂— | H | |
| 10 | pyrrolidino (N ring) | —CH₂— | —CH₂—CH₂— | —CH₂— | H | |

-continued

| R¹ | A | B | X | Zn | M.p. [°C.] |
|---|---|---|---|---|---|
| 11 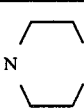 | —CH₂— | —CH₂—CH₂— | —CH₂— | H | |
| 12 —CCl₂CH₃ | —CH₂— | —CH₂—CH₂— | —CH₂— | H | |
| 13 —CH₂OCH₃ | —CH₂— | —CH₂—CH₂— | —CH₂— | H | |
| 14 O-t-C₄H₉ | —CH₂— | —CH₂—CH₂— | —CH₂— | H | |
| 15 S-n-C₃H₇ | —CH₂— | —CH₂—CH₂— | —CH₂— | H | |
| 16 N(OCH₃)CH₃ | —CH₂— | —CH₂—CH₂— | —CH₂— | 4-Cl | 102–103 |
| 17 C₂H₅ | —CH₂— | —CH₂—CH₂— | —CH₂— | 4-Cl | 121–122 |
| 18 N(OCH₃)CH₃ | —CH₂— | —CH₂—CH₂— | —CH₂— | 4-F | 111–114 |
| 19 C₂H₅ | —CH₂— | —CH₂—CH₂— | —CH₂— | 4-t-C₄H₉ | |
| 20 N(CH₃)₂ | —CH₂— | —CH₂—CH₂— | —CH₂— | 4-F | 145–148 |
| 21 N(CH₃)₂ | —CH₂— | —CH₂—CH₂— | —CH₂— | 4-Cl | |
| 22 N(CH₃)₂ | —CH₂— | —CH₂—CH₂— | —CH₂— | 4-CH₃ | |
| 23 N(CH₃)₂ | —CH₂— | —CH₂—CH₂— | —CH₂— | 4-OCH₃ | |
| 24 N(OCH₃)CH₃ | —CH₂— | —CH₂—CH₂— | —CH₂— | 4-OCH₃ | 106–108 |
| 25 C₂H₅ | —CH₂— | —CH₂—CH₂— | —CH₂— | 4-OCH₃ | 139–141 |
| 26 C₂H₅ | —CH₂— | —CH₂—CH₂— | —CH₂— | 4-CH₃ | |
| 27 N(OCH₃)CH₃ | —CH₂— | —CH₂—CH₂— | —CH₂— | 4-CH₃ | 122–124 |
| 28 N(OCH₃)CH₃ | —CH₂— | —CH₂—CH₂— | —CH₂— | 3,4-(CH₃)₂ | |
| 29 N(OCH₃)CH₃ | —CH₂— | —CH₂—CH₂— | —CH₂— | 4-t-C₄H₉ | |
| 30 N(OCH₃)CH₃ | —CH₂— | —CH₂—CH₂— | —CH₂— | 3-CF₃ | |
| 31 N(OCH₃)CH₃ | —CH₂— | —CH₂—CH₂— | —CH₂— | 4-OCHF₂ | |
| 32 N(OCH₃)CH₃ | —CH₂— | —CH₂—CH₂— | —CH₂— | 4-O—n-C₆H₁₃ | |
| 33 N(OCH₃)CH₃ | —CH₂— | —CH₂—CH₂— | —CO— | 4-Cl | 129–131 |
| 34 C₂H₅ | —CH₂— | —CH₂—CH₂— | —CO— | 4-Cl | 110–112 |
| 35 N(CH₃)₂ | —CH₂— | —CH₂—CH₂— | —CO— | 4-Cl | |
| 36 N(CH₃)₂ | —CH₂— | —CH₂—CH₂— | —CO— | 4-F | |
| 37 C₂H₅ | —CH₂— | —CH₂—CH₂— | —CO— | 4-CH₃ | 108–110 |
| 38 N(CH₃)₂ | —CH₂— | —CH₂—CH₂— | —CO— | 4-OCH₃ | |
| 39 N(CH₃)₂ | —CH₂— | —CH₂—CH₂— | —CO— | H | |
| 40 C₂H₅ | —CH₂— | —CH₂—CH₂— | —CO— | H | 130–132 |
| 41 C₂H₅ | —CH₂— | —CH₂—CH₂— | —CH₂— | 4-F | 117–119 |
| 42 C₂H₅ | —CH₂— | —CH₂—CH₂— | —CH₂— | 3,4-(CH₃)₂ | |
| 43 C₂H₅ | —CH₂— | —CH₂—CH₂— | —CH₂— | 3-CF₃ | |
| 44 N(OCH₃)CH₃ | —CH₂— | —CH₂—CH₂— | —CH₂— | H | |
| 45 N(OCH₃)CH₃ | —CH₂— | —CH₂—CH₂— | —CH(OH) | H | oil |
| 46 N(OCH₃)CH₃ | —CH₂— | —CH₂—CH₂— | —CO— | 4-F | |
| 47 N(OCH₃)CH₃ | —CH₂— | —CH₂—CH₂— | —CO— | 4-CH₃ | 129–131 |
| 48 N(OCH₃)CH₃ | —CH₂— | —CH₂—CH₂— | —CO— | 4-OCH₃ | 118–120 |
| 49 N(OCH₃)CH₃ | —CH₂— | —CH₂—CH₂— | —CO— | 3,4-Cl₂ | |
| 50 N(OCH₃)CH₃ | —CH₂— | —CH₂—CH₂— | —CO— | 3-Cl | |
| 51 N(OCH₃)CH₃ | —CH₂— | —CH₂— | —CO— | H | 111–113 |
| 52 N(OCH₃)CH₃ | —CH₂CH₂CH₂CH₂— | —CH₂—CH₂— | —CO— | H | oil |
| 53 C₂H₅ | —CH₂CH₂CH₂— | —CH₂—CH₂— | —CO— | H | |
| 54 N(OCH₃)CH₃ | —CH₂—CH₂—CH₂— | —CH₂— | —CH₂— | H | |
| 55 C₂H₅ | —CH₂—CH₂—CH₂— | —CH₂— | —CH₂— | H | |
| 56 N(CH₃)₂ | —CH₂—CH₂—CH₂— | —CH₂— | —CH₂— | H | |
| 57 N(CH₃)₂ | —CH₂— | —CH₂— | —CH₂— | —CH₂— | H |
| 58 C₂H₅ | —CH₂— | —CH₂— | —CH₂— | H | |
| 59 N(OCH₃)CH₃ | —CH₂— | —CH₂— | —CH₂— | H | 70–72 |
| 60 N(OCH₃)CH₃ | —CH₂—CH(CH₃)—CH₂— | —CH₂—CH₂— | —CH₂— | H | |
| 61 C₂H₅ | —CH₂—CH(CH₃)—CH₂— | —CH₂—CH₂— | H | | |
| 62 N(CH₃)₂ | —CH₂—CH(CH₃)—CH₂— | —CH₂—CH₂— | —CH₂— | H | |
| 63 N(CH₃)₂ | —CH₂CH₂CH₂— | —CH₂—CH₂— | —CH₂— | H | |
| 64 N(OCH₃)CH₃ | —CH₂CH₂CH₂— | —CH₂—CH₂— | —CH₂— | H | 65–67 |
| 65 C₂H₅ | —CH₂CH₂CH₂— | —CH₂—CH₂— | —CH₂— | H | oil |
| 66 C₂H₅ | —(CH₂)₅— | —CH₂—CH₂— | —CH₂— | H | |
| 67 N(OCH₃)CH₃ | —(CH₂)₅— | —CH₂—CH₂— | —CH₂— | H | |
| 68 N(CH₃)₂ | —(CH₂)₅— | —CH₂—CH₂— | —CH₂— | H | |
| 69 OCH₃ | —CH₂— | —CH₂—CH₂— | —CH₂— | 4-OCH₃ | 147–149 |
| 70 N(OCH₃)CH₃ | —CH₂— | —CH₂—CH₂— | —CO— | H | 108–110 |
| 71 N(CH₃)₂ | —CH₂— | —CH₂— | —CO— | H | 168–170 |
| 72 C₂H₅ | —CH₂— | —CH₂—CH₂— | —CH(OH)— | H | 126–128 |

The compounds of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions, or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talcs, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 25 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 3 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 17 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 33 is intimately mixed with 97 parts by weight of particulate kaolin. A dust is obtained containing 3% by weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 1 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combated and their growth stage, and varies from 0.05 to 5 kg/ha and more, but is preferably from 0.1 to 3.0 kg/ha.

The herbicidal action of compounds of the formula I is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. For this treatment, either plants which had been sown directly in the pots and grown there were selected, or plants which had been grown from seedlings and were transplanted to the pots a few days before treatment. No covers were placed on the pots in this treatment method. The application rates for postemergence treatment were for example 0.125, 1.0 or 2.0 kg of active ingredient per hectare.

The pots were set up in the greenhouse—species from warmer areas at from 20° to 35° C., and species from moderate climates at 10° to 20° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were *Alepecurus myosuroides, Amaranthus retroflexus,* Amaranthus spp., *Cassia tora, Chenopodium album,* Chrysanthemum spp., *Euphorbia geniculata, Galium aparine,* Ipomoea spp., *Lamium amplexicaule, Sesbania exaltata, Sida spinosa, Sinapis alba, Solanum nigrum,* and *Triticum aestivum.*

On preemergence application of 3.0 kg/ha, for example compounds nos. 1, 2, 3 and 33 had a good herbicidal action on *Sinapis alba.*

On postemergence application of 0.125 kg/ha, for instance compound no. 1 combatted unwanted broad-leaved plants. Wheat was only slightly damaged, and then only initially. A good postemergence action was also exhibited for example by compound no. 33 at 1.0 kg/ha, and by compounds nos. 2 and 17 at 2.0 kg/ha.

In view of the numerous application methods possible, the compounds according to the invention, or agents containing them, may be used in a large number of crop plants for removing unwanted plants.

To increase the spectrum of action and to achieve synergistic effects, the aniline derivatives of the formula I may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, triazinones, uracils, benzofuran derivatives, etc.

It may also be useful to apply the compounds of the formula I, either alone or in combination with other herbicides, in admixture with other crop protection agents, e.g., agents for combatting pests or phytopathogenic fungi or bacteria. The compounds may also be mixed with solutions of mineral salts used to remedy nutritional or trace element deficiencies. Nonphytotoxic oils and oil concentrates may also be added.

We claim:

1. An aniline derivative of the formula

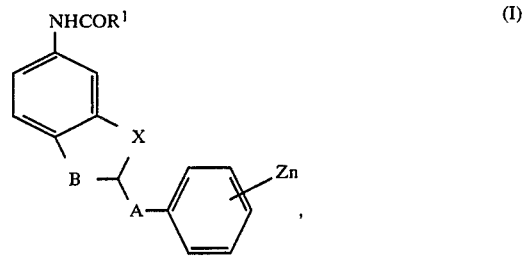

where $R^1$ is a radical selected from the group consisting of $C_1$-$C_4$-alkoxy, $C_1$-$C_4$-alkylthio, $C_1$-$C_4$-alkyl which is unsubstituted or substituted by halogen or by $C_1$-$C_5$-alkoxy, $C_3$-$C_6$-cycloalkyl, $C_3$-$C_6$-cycloalkoxy, and the radical —$NR^2R^3$ where $R^2$ and $R^3$ are each independently a substituent selected from the group consisting of hydrogen, $C_1$-$C_4$-alkyl, $C_1$-$C_4$-alkoxy, $C_3$-$C_6$-cycloalkyl and $C_3$-$C_6$-cycloalkoxy, or where $R^2$ and $R^3$ together form an alkylene chain of not more than 6 carbon atoms which is unsubstituted or substituted by methyl and may or may not contain oxygen as a chain member, X is methylene, —CH(OH)— or —CO—, A is an alkylene chain of 1 to 5 carbon atoms which is unsubstituted or substituted by alkyl of 1 to 5 carbon atoms, B is methylene or dimethylene which is unsubstituted or substituted by alkyl of 1 to 3 carbon atoms, Z is hydrogen, halogen, $C_1$-$C_6$-alkyl, $C_1$-$C_6$-alkoxy, $C_1$-$C_6$-haloalkyl or $C_1$-$C_6$-haloalkoxy, and n is 1, 2 or 3.

2. An aniline derivative of the formula I as claimed in claim 1, where $R^1$ is —$N(CH_3)(OCH_3)$, A is methylene, X is methylene, B is methylene, Z is halogen, hydrogen or $C_1$-$C_4$-alkyl, and n is 1.

3. An aniline derivative of the formula I as claimed in claim 1, where $R^1$ is —$N(CH_3)(OCH_3)$, A is methylene, X is methylene, B is dimethylene, Z is chlorine, hydrogen or methyl, and n is 1.

4. An aniline derivative of the formula I as claimed in claim 1, where $R^1$ is —$N(CH_3)(OCH_3)$, A is methylene, X is methylene, B is dimethylene, Z is hydrogen, and n is 1.

5. A herbicide containing inert additives and an aniline derivative of the formula I as claimed in claim 1.

6. A herbicide as claimed in claim 5, containing from 0.1 to 95 wt% of the aniline derivative of the formula I as claimed in claim 1.

7. A herbicide as claimed in claim 5, where $R^1$ is —$(CH_3)(OCH_3)$, A is methylene, X is methylene, B is methylene, Z is halogen, hydrogen or $C_1$-$C_4$-alkyl and n is 1.

8. A herbicide as claimed in claim 5, where $R^1$ is —$N(CH_3)(OCH_3)$, A is methylene, X is methylene, B is dimethylene, Z is chlorine, hydrogen or methyl, and n is 1.

9. A process for combatting unwanted plant growth, wherein a herbicidally effective amount of an aniline derivative of the formula I as claimed in claim 1 is allowed to act on the plants or their location.

* * * * *

UNITED STATES PATENT AND TRADEMARK OFFICE
CERTIFICATE OF CORRECTION

PATENT NO. : 4,569,689
DATED : February 11, 1986
INVENTOR(S) : Ulrich SCHIRMER et al.

It is certified that error appears in the above—identified patent and that said Letters Patent is hereby corrected as shown below:

IN THE CLAIMS:

Claim 7, col. 12, line 54, change "$-(CH_3)(OCH_3)$" to -- $-N(CH_3)(OCH_3)$ --

Signed and Sealed this

Thirteenth Day of May 1986

[SEAL]

Attest:

DONALD J. QUIGG

Attesting Officer

Commissioner of Patents and Trademarks